United States Patent [19]

Smith et al.

[11] 4,090,392
[45] May 23, 1978

[54] AUTOMATIC GAS ANALYZER SYSTEM

[75] Inventors: Isaac L. Smith, Baton Rouge, La.;
Clarence I. Glassbrook, Swedesboro, N.J.

[73] Assignee: Ethyl Corporation, Richmond, Va.

[21] Appl. No.: 820,847

[22] Filed: Aug. 1, 1977

[51] Int. Cl.² .............................................. G01N 1/26
[52] U.S. Cl. ............................................. 73/421.5 R
[58] Field of Search .......... 73/1 G, 421.5 R, 421.5 A, 73/421 B

[56] References Cited

U.S. PATENT DOCUMENTS

| | | | |
|---|---|---|---|
| 3,043,145 | 7/1962 | Hoffman | 73/421.5 |
| 3,359,784 | 12/1967 | Jorre | 73/1 G |
| 3,921,456 | 11/1975 | Newcomb et al. | 73/421.5 R |
| 3,927,670 | 12/1975 | Turney et al. | 73/421.5 R |

Primary Examiner—S. Clement Swisher
Attorney, Agent, or Firm—Donald L. Johnson; John F. Sieberth; James M. Pelton

[57] ABSTRACT

A method and apparatus for automatically sampling and analyzing a multitude of sample points from an area, using one analyzer and a control system to sequentially send samples for analysis.

8 Claims, 3 Drawing Figures

AUTOMATIC GAS ANALYZER SYSTEM

BACKGROUND OF THE INVENTION

This invention relates to a method and apparatus for automatically obtaining and analyzing fluid samples, particularly samples of gases. More particularly, this invention concerns a system or apparatus for collection of and supply to the analyzer of fresh sample from a relatively distant point whereby the sample obtained has not remained stagnant in sample lines or collection vessels for significant periods of time. Also, the present invention relates to a method for sequentially analyzing a number of samples and a method for automatically providing the proper sample at the proper time.

The provisions, rules and regulations imposed by various governmental regulatory agencies have made it necessary to limit worker exposure to various elements and compounds in their work environment. This necessitates complete knowledge of the presence of one or more elements or compounds in the atmosphere. Comprehensive and expensive sampling programs have been employed by the affected industries to accomplish this. However, such programs require a number of analytical personnel or technicians to acquire and analyze the samples obtained. In many instances, the analyzers have been automated to provide for fairly quick and accurate analysis, while sample collection and interfacing with the analyzer has not kept pace with developments in the automation of analyzers.

Not only government action, but industry concern for safety and protection of workers and equipment have led to development of on-site or portable samplers or analyzers to augment process control instrumentation for warning of unusually high levels of certain elements or compounds, presaging leaks, eminent equipment failure or worker exposure to dangerous levels of certain elements or compounds.

The advent of automatic or computer controllable analyzers has preceded the development of adequate sample systems which do not require unusually large amounts of manpower for sample collection or high capital investment for numerous in-place automatic analyzers. Accordingly, there is a need for a sample collection apparatus and method which can be keyed to an automatic analyzer, which can provide fresh samples, which can perform reliably, which can perform rapidly, and which can cover a multitude of sample points. The present invention fills this need.

SUMMARY OF THE INVENTION

In accord with the present invention, there is provided an automatic fluid sample selection apparatus comprising, in combination, an array of sample lines having one end fitted with a particulate filter and located at the site to be sampled and the other end of said sample lines connected to the inlet of a corresponding number of sample pumps, the discharge of each of said pumps being connected by appropriate lines to a first sample vent manifold through a pressure controlling valve and to a first control valve, whereby a predetermined pressure set on said pressure controlling valve at a level such that when the valve is opened, flow goes through the valve only and when said first control valve is closed, flow goes through the pressure controller into said first vent manifold without back pressure damage to said pump, at least two of said first control valves being connected by appropriate conduit to an array of second control valves numbering at least one-half of the number of said first control valves, said second control valves being connected to a second sample vent manifold and to an automatic analyzer manifold whereby each of said second control valves normally discharges into said second sample vent manifold and on command switches the sample flow to said automatic analyzer manifold for analysis by the automatic analyzer, whereby a signal timing means sequentially operates said first and said second control valves such that sample from one of said sample lines is freshly pumped to said first control valve and out said first sample vent manifold until upon sequential command of said timing means the sample is pumped to said second control valve with continuous flow to said second control valve by means of said second sample vent manifold until said second control valve is sequentially commanded to send the sample to said automatic analyzer manifold and to said automatic analyzer for analysis.

DESCRIPTION OF THE PREFERRED EMBODIMENTS

Figure 1:
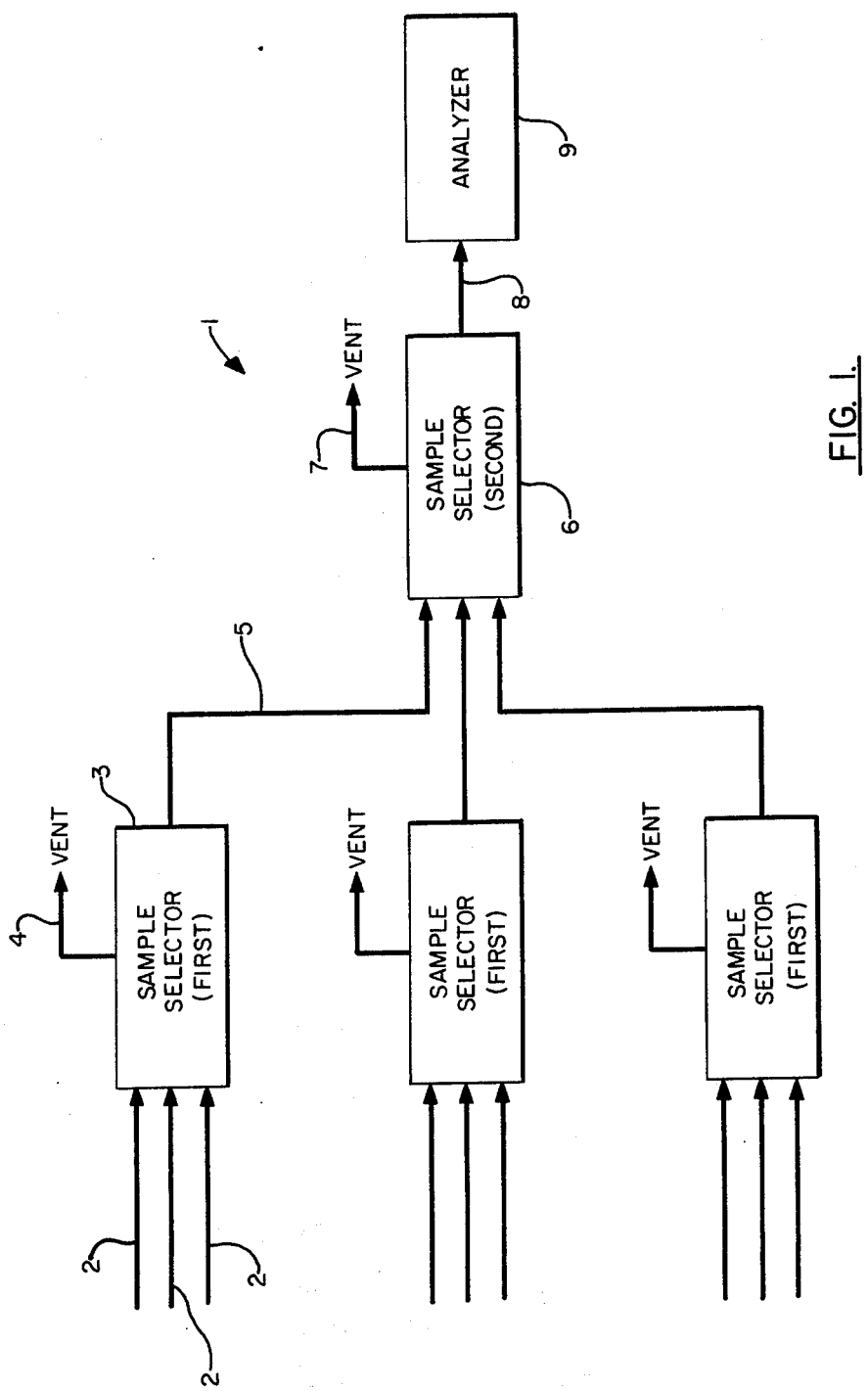
FIG. 1 is a sample schematic representation of the basic concept of the invention in which a multitude of sample lines are led into a sample selector means and one sample is selected and led to another sample selector for selection of the sample for analysis. Those sample lines not selected are vented making fresh sample continuously available to the nearest point possible in the system to the analyzer.

The present invention can be more readily understood from reference to the drawings. In FIG. 1, there is schematically illustrated the concept of the invention, in which the sample collection and selection apparatus generally indicated by 1, has a number of identical sample lines 2 leading from the point to be sampled (not shown) to a first sample selector means 3 having a vent outlet line 4 and a selected sample line 5 which connects said sample selector 3 to a second sample selector 6, also having the second sample vent 7 and a second selected sample line 8 for supplying the sample to be analyzed to automatic analyzer 9. In a similiar manner, several sets of identical sample lines can be attached to another identical first sample selector which is in turn connected to the second sample selector 6 so that a multitude of sample lines can be sequentially switched to one clear path to the analyzer while the remaining sample lines continue to draw in fresh samples of the fluid to be analyzed and route them to the vent until it is time for switching the analyzer to any particular sample line.

One skilled in the art will clearly see that such a system can be operated by manually activating the sample selectors but it is clearly advantageous to use automatic sample selectors. These may be any type of valve controlling flow through the line which are adapted for automatic actuation, for example, solenoid valves commercially available can be employed.

The advantage of the sample system of this invention is that the multiple sample lines represented in FIG. 1 continuously move fresh sample through the lines and no stagnant lines are employed, thus assuring an accurate and up-to-date sample.

The sample lines employed can be any material which is inert to the environment, compound or element to be sampled. Materials such as metal tubing, e.g., stainless steel, copper, mild steel and the like; plastic tubing, e.g., nylon, polyvinyl chloride, polyvinyl fluoride, teflon and the like; and natural or synthetic rubber can be used so long as the tubing can withstand the environment in which it is used, is substantially inert to the sample fluid and has substantially no accumulative properties or "memory" for the sample which would give inaccurate analysis.

Many analyzers can be employed with the sample collection and selection system of this invention. Depending upon the situation encountered, various items such as gas chromatographic, atomic absorption spectrophotometric, infra-red, nuclear magnetic resonance and the like can be used.

Figure 2:
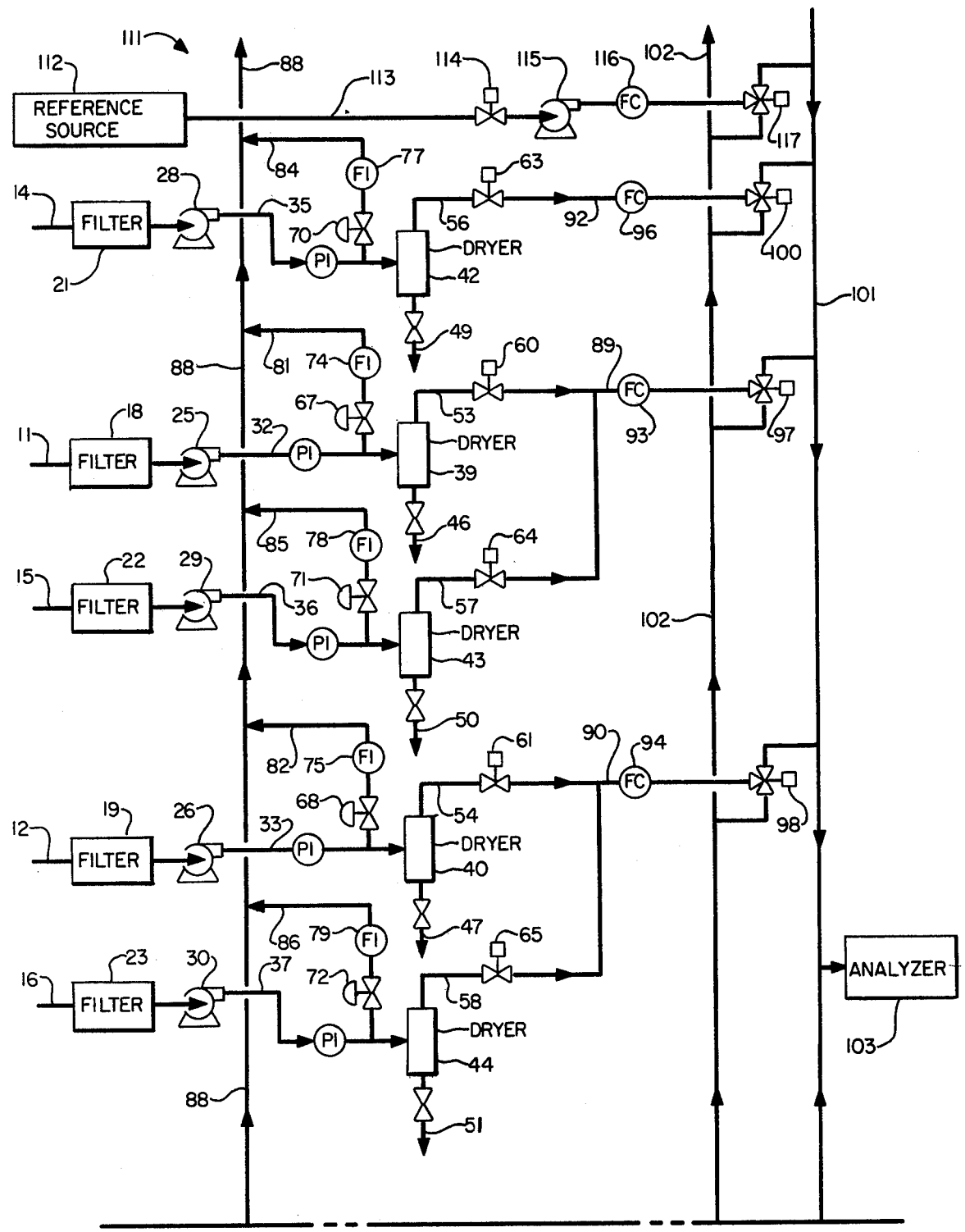
FIG. 2 is a detailed schematic process flow diagram of a practical apparatus according to the invention with the electronics not shown.
Figure 2A:
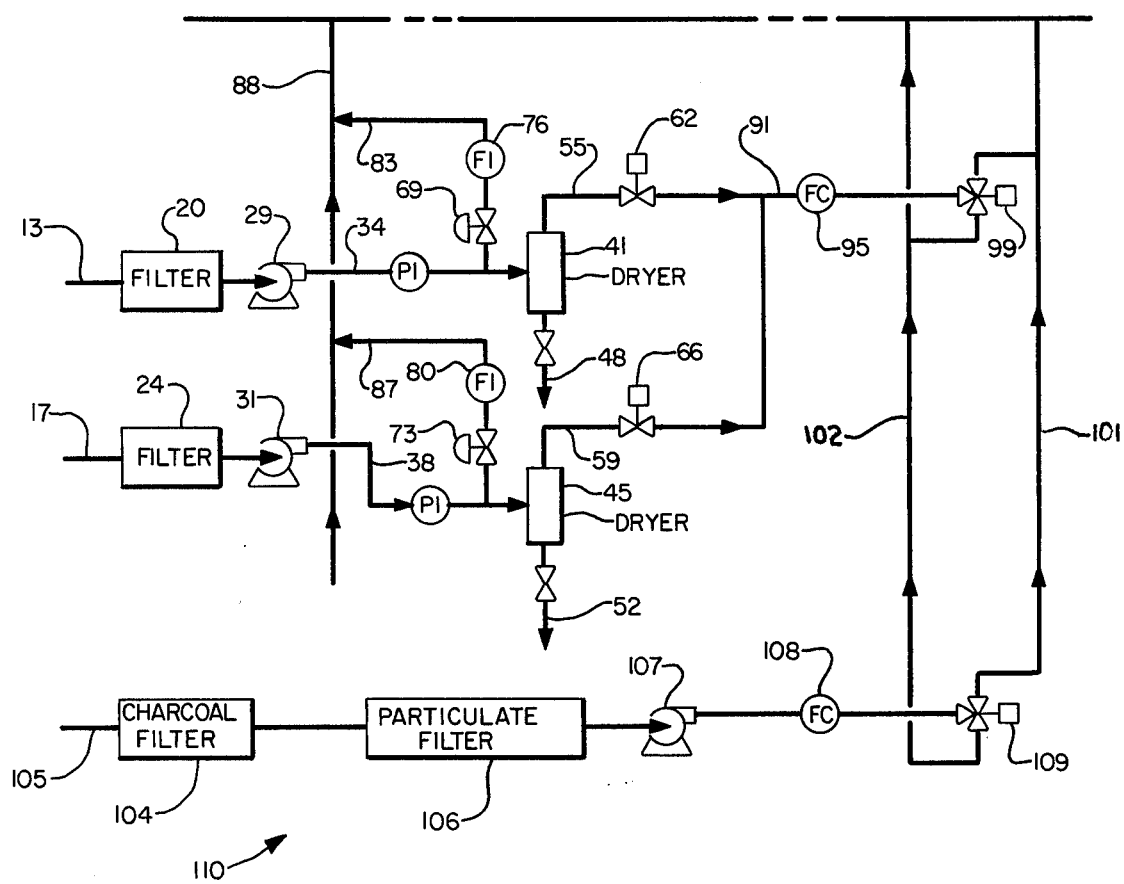

Referring to FIG. 2, there is illustrated a practical system for analysis of air samples by an automatic atomic absorption spectrophotometer. The element to be analyzed by this type of instrument depends upon the source of ultraviolet light employed. It may use a hollow cathode lamp or an electrodeless discharge lamp source in the unit in which the cathode of the lamp contains the element of interest and the instrument measures the difference between the absorption of the light striking the sample and that by-passing the sample through a prism and reads out the results in engineering units, such as micrograms per cubic meter. For illustration, in atomic absorption analysis a sample is heated to a high temperature by burning it in a flame. The flame breaks up the chemical bonds between the molecules enabling individual atoms to float freely in a sample area. In this condition, atoms can absorb ultraviolet or visible radiation. The wave length bands in which each specific element can absorb energy are very narrow and are different for every element. The ultraviolet wave length of 283.4 nanometers is used in this application, which is specific for the element lead. The flame uses acetylene as a fuel and compressed air as the oxidant. If one wishes to determine the concentration of lead, for example, he passes the light from a source through the flame. The source is an electrodeless discharge lamp whose cathode contains the element of interest — in this case, lead. A certain portion of the light striking the flame will be absorbed, depending on the concentration of lead in the sample. The instrument measures the amount of absorption. Modern atomic absorption spectrophotometers can be set to read out the results directly into concentration values. In this case, it is micrograms per cubic meter. To obtain the necessary stability, accuracy and sensitivity in the instrument, the electrodeless discharge lamp source is alternately switched to pass through the flame and also pass around the flame by a system of prisms and mirrors. After passing either through or around the flame, the light from the source is received by a photomultiplier detector which detects the light intensity. The electronics compares the differential intensities between the beam that goes through the flame and the beam that goes around the flame and uses this information to determine the actual concentration of the sample.

As illustrated in more detail in FIG. 2, a preferred embodiment of this invention includes a series of sample lines, Numbers 11 through 17, which are connected to particulate filters 18 through 24, respectively. Filters 18 through 24, respectively, are connected to the suction sides of pumps 25 through 31. The discharge from pumps 25 through 31 is connected by means of lines 32 through 38, respectively, to knock-out pots or dryers 39 through 45, respectively, which remove any moisture picked up by the sample or accumulated in the sample lines 11 through 17 or pump discharge lines 32 through 38. Any moisture recovered is drained through drain lines 46 through 52 attached, respectively, to dryers 39 through 45.

From dryers 39 through 45, the sample goes through lines 53 through 59 to first control valves 60 through 66, respectively. In the event that all first control valves 60 through 66 are closed, pressure would build up and damage pumps 25 through 31 and also the sample would be deadheaded until the respective first control valve was opened. To alleviate the pressure and prevent sample deadspace, pressure control valves 67 through 73, respectively, are connected to pump discharge lines 32 through 38. The pressure control valves 67 through 73 are set high enough so that opening of one of the first control valves 60 through 66 will allow flow only through the respective first control valve, but low enough so that on closing of one of the first control valves 60 through 66 the pressure in the respective pump discharges 32 through 38 will not exceed pressures damaging to pumps 25 through 31. The actual pressures set for pressure control valves 67 through 73 will depend on the type of pumps used, the line size and material, and the ratings of the first control valves, etc. Practically speaking, pressures of about 10 psig are sufficient to accomplish the purposes stated. From pressure control valves 67 through 73, respectively, the unused sample relieves through flow indicators 74 through 80, respectively, and sample relief lines 81 through 87, respectively, into vent manifold 88 and ultimately to either the atmosphere or to waste treatment facilities, not shown.

If one of the first control valves 60 through 66 is open, then the sample goes through lines 89 through 92, respectively, flow indicating controllers 93 through 96, respectively, and into second control valves 97 through 100, respectively. Second control valves are three-way valves which in one configuration pass the flow to an analyzer manifold 101 and in the other configuration pass the flow to a second vent manifold 102. From analyzer manifold 101, the sample goes to the analyzer 103, for example, the burner of an atomic absorption spectrophotometer, which reads the sample.

In the embodiment shown in FIG. 2, the use of an atomic absorption spectrophotometer requires two additional sample lines — a zero sample and a reference sample. These two sample trains are also connected to analyzer manifold 101 and second vent manifold 102. The zero sample, having nothing but air or oxygen for the burner or other inert gas providing none of the element to be measured is a baseline for analyzer 103. The zero sample train 110 has activated charcoal filter 104 in zero sample line 105 as well as particulate filter 106, pump 107, flow indicating controller 108 and three-way control valve 109. Since the zero reference system is not part of a multitude of samples, it does not require the use of double control valves.

In a similar vein, the reference sample train 111 provides a known amount of the element or compound to be analyzed for calibration of the analyzer. It contains a source of reference sample 112 which is pulled through reference sample line 113 and control valve 114 through pump 115, flow indicating controller 116 and three-way control valve 117 which is connected to analyzer manifold 101 and second vent manifold 102.

In operation, the system illustrated in FIG. 2 can be described by reference to the operation of a typical cycle for analyzing a number of samples. The preferred control valves are solenoid energized valves. Although other kinds are useful, these provide rapid and automatic response to the command signal.

At the beginning of each sample cycle (time equals zero), all first and second control valves are deenergized. In this condition, sample flow from pump 107 through flow indicating controller 108, and deenergized control valve 109 is fed directly into the sample manifold 101 and to the analyzer 103 for analysis. Since the suction of pump 107 contains an activated charcoal filter 104, zero reference air is being fed to the analyzer 103. This is used to zero calibrate the analyzer 103 and to sustain the burner flame during periods when no sample is being supplied.

The system operates sequentially with overlap between operations of the various control valves. The sequential operation is as follows:

| Time (Seconds Into Cycle) | Event |
| --- | --- |
| 0000.0 | Reset - start new cycle; all control valves are deenergized. With all control valves deenergized, the burner analyzes zero air from control valve 109 and the charcoal filter 104. |
| 0000.2 | Control valve 114 energized - this allows pump 115 to pull sample from the reference sample source 112 and pump it through flow indicating controller 116 into control valve 117. Since control valve 117 is deenergized, this sample is bypassed to vent manifold 102, but kept fresh up to that point. |
| 0015.0 | First control valve 60 energized - this allows pump 28 to pump through flow indicating controller 93 into deenergized second control valve 97, making sample from point No. 11 fresh up to second control valve 98, where it is bypassed to vent manifold 102. |
| 0030.0 | First control valve 61 energized - this allows pump 26 to pump sample through flow indicating controller 94 into deenergized second control valve 98, making sample from point No. 12 fresh up to second control valve 98, where it is bypassed to vent manifold 102. |
| 0035.0 | Analyzer is commanded to auto zero on sample from charcoal filter. |
| 0040.0 | Analyzer reads "zero" sample. |
| 0045.0 | First control valve 62 energized - this allows pump 27 to pump sample through flow indicating controller 95 into deenergized second control valve 99, making sample from point No. 13 fresh up to second control valve 99 where it is bypassed to vent manifold 102. |
| 0047.0 | Auto concentrate cycle begins. Control valve 117 energized - this sends sample from reference sample source 112 into analyzer 103 for analysis to automatically calibrate the analyzer 103 to a known concentration. Analyzer 103 will see this sample for eight seconds before the auto concentrate command is given. Control valve 109 energized - this blocks flow of zero sample into burner. Control valve 109 is connected so that its deenergized position allows flow to the sample manifold 102 to continue burner air in the event that power to the control valves is lost. |
| 0055.0 | Auto concentrate command given to analyzer 103. |
| 0059.5 | Analyzer 103 reads auto concentrate data. |
| 0065.0 | Second control valve 97 energized - this sends sample from point No. 11 into the analyzer 103 for analysis. The analyzer 103 analyzes the point for 8 seconds to allow the system to stabilize before read command is given. Second control valve 117 |

| Time (Seconds Into Cycle) | Event |
| --- | --- |
| | and control valve 114 deenergized - this blocks flow from reference sample source into burner. |
| 0073.0 | Read command is given analyzer 103 to read sample from point No. 11. |
| 0075.0 | First control valve 63 energized - this allows pump 28 to pump sample through flow indicating controller 96 into deenergized second control valve 100, making sample No. 14 fresh up to second control valve 100, where it is bypassed to vent. |
| 0080.0 | Second control valve 98 energized - this sends sample from point No. 12 into analyzer 103 for analysis. The analyzer 103 analyzes the point for 8 seconds to allow the system to stabilize before the read command is given. Second control valve 97 deenergized this blocks flow from sample point No. 11 to the burner. |
| 0088.0 | Read command is given analyzer to read sample point No. 12. |

The sequence continues until sample points have been analyzed. Then, the electronics resets to zero and a new cycle begins. For each sample point, a control valve corresponding to that sample point is opened 50 seconds prior to the time that th point is actually switched into the analyzer. This time is used to make sure that the lines are purged and the sample is fresh up to the corresponding control valve on the sample manifold 101 before the analyzer 103.

The electronics which command the cycle can be any logic family, for example, a transistor-transistor logic family or a microcomputer system which is designed to operate the present invention as described hereinabove. Control functions for the operation of the analyzer, the control valves in the sample system, a data readout system and an alarm system to call attention to the high concentration of the particular element analyzed is contained in an electronic control panel. One skilled in the electronics art can imagine numerous means to supply the necessary control functions for the sample system of this invention.

Having described the invention, it is clear that one skilled in the art can envision numerous changes and variations therein within the concept of the invention. Therefore, it is desired to limit the invention only within the lawful scope of the appended claims.

What is claimed is:

1. An automatic fluid sample selection apparatus comprising, in combination, an array of sample lines having one end fitted with a particulate filter and located at the site to be sampled and the other end of said sample lines connected to the inlet of a corresponding number of sample pumps, the discharge of each of said pumps being connected by appropriate lines to a first sample vent manifold through a pressure controlling valve and to a first control valve, whereby a predetermined pressure is set on said pressure controlling valve at a level such that when said first control valve is opened, flow goes through said first control valve only and when said first control valve is closed, flow goes through the pressure controller into said first vent manifold without back pressure damage to said pump, at least two of said first control valves being connected by appropriate conduit to an array of second control valves numbering at least one-half of the number of said first control valves, said second control valves being connected to a second sample vent manifold and to an automatic analyzer manifold whereby each of said second control valves normally discharges into said second sample vent manifold and on command switches the sample flow to said automatic analyzer manifold for analysis by the automatic analyzer, whereby a signal timing means sequentially operates said first and said second control valves such that sample from one of said sample lines is freshly pumped to said first control valve and out said first sample vent manifold until upon sequential command of said timing means the sample is pumped to said second control valve with continuous flow to said second control valve by means of said second sample vent manifold until said second control valve is sequentially commanded to send the sample to said automatic analyzer for analysis.

2. The apparatus of claim 1 wherein said first control valve is a two-way solenoid valve.

3. The apparatus of claim 1 wherein said second control valve is a three-way solenoid valve.

4. The apparatus of claim 1 wherein said apparatus has two first control valves connected to each second control valve.

5. A method for automatically supplying sequentially a number of gas samples for analysis using an apparatus including an analyzer, a source of zero sample, connected to said analyzer, a reference source for calibrating said analyzer and a number of sample sources, each of which has serially connected in the sample line a filter, a pump, a pressure controlled vent means and a first control valve and having a number of said sample sources connected to a second control valve which in turn is connected to a second vent means and to the analyzer by means of a sample manifold, said method comprising the steps of:

(a) at the beginning of each analysis cycle, said source of zero sample is conducted to said analyzer while the other sources are vented;

(b) at a predetermined time after analysis of said source of zero sample, conducting said reference source to said analyzer for calibration with the known amount of sample while the other sources are vented, (c) sequentially activating the control valves so that one sample at a time passes the first and second control valves to be analyzed while all other sources are vented, and (d) after all sample sources have been analyzed, recycling the apparatus to begin said method again until stopped.

6. The method of claim 5 wherein said analyzer is an atomic absorption spectrophotometer adapted for automatic read and output functions.

7. The method of claim 5 wherein a sample is analyzed every fifteen seconds.

8. The method of claim 5 wherein the sequential operation of said first and said second control valves allows one of said sample sources to flow to said second vent means through said second control valve prior to analysis while the other sample sources connected to the same second control valve are blocked by their respective first control valves and vented through their respective pressure controlled vent means.

* * * * *